(12) United States Patent
Staunton et al.

(10) Patent No.: US 9,002,451 B2
(45) Date of Patent: Apr. 7, 2015

(54) IMPLANTABLE ELECTRODE ARRAY ASSEMBLY WITH EXTRACTION SLEEVE/TETHER

(75) Inventors: Douglas A. Staunton, Texas Township, MI (US); John J. Janik, Hudsonville, MI (US); Richard F. Huyser, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 136 days.

(21) Appl. No.: 13/445,660

(22) Filed: Apr. 12, 2012

(65) Prior Publication Data
US 2012/0203246 A1 Aug. 9, 2012

Related U.S. Application Data

(63) Continuation of application No. 12/566,720, filed on Sep. 10, 2009, now abandoned.

(60) Provisional application No. 61/096,196, filed on Sep. 11, 2008.

(51) Int. Cl.
*A61N 1/00* (2006.01)
*A61N 1/05* (2006.01)
*A61N 1/36* (2006.01)
*A61N 1/372* (2006.01)
*A61N 1/378* (2006.01)

(52) U.S. Cl.
CPC ........... *A61N 1/0551* (2013.01); *A61N 1/36071* (2013.01); *A61N 1/37217* (2013.01); *A61N 1/3787* (2013.01)

(58) Field of Classification Search
USPC ................. 607/45–46, 116–118, 129, 60
See application file for complete search history.

(56) References Cited

U.S. PATENT DOCUMENTS

| | | | |
|---|---|---|---|
| 2005/0085870 A1* | 4/2005 | Goroszeniuk | 607/46 |
| 2007/0179581 A1* | 8/2007 | Dennis et al. | 607/119 |
| 2009/0033769 A1 | 2/2009 | Nagaoka et al. | |
| 2009/0293270 A1 | 12/2009 | Brindley et al. | |
| 2010/0063568 A1 | 3/2010 | Staunton et al. | |
| 2011/0077660 A1 | 3/2011 | Janik et al. | |

FOREIGN PATENT DOCUMENTS

WO 2008/080073 A2 7/2008

* cited by examiner

*Primary Examiner* — Catherine Voorhees
*Assistant Examiner* — Roland Dinga

(57) ABSTRACT

An implantable electrode array including a carrier on which plural electrodes are disposed. Also disposed on the carrier is an array antenna over which signals are wirelessly received. A tether is connected to the carrier. A tether antenna is attached to the tether. After the electrode array is implanted, during a trial period instructions and power are transmitted to the array antenna over the tether antenna. If the trial is successful, the tether is disconnected from the electrode array. If the trial is not successful and extraction of the array is necessary, extraction is accomplished by pulling on the tether. Electrode array removal may be facilitated by the pulling of the array into an extraction tube disposed over the tether.

23 Claims, 16 Drawing Sheets

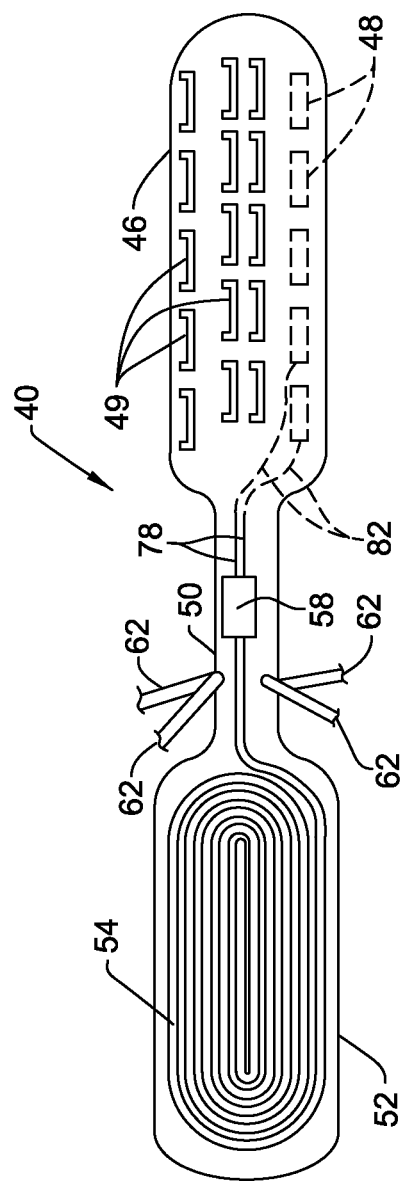

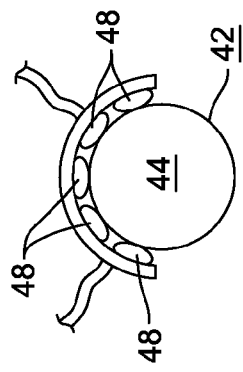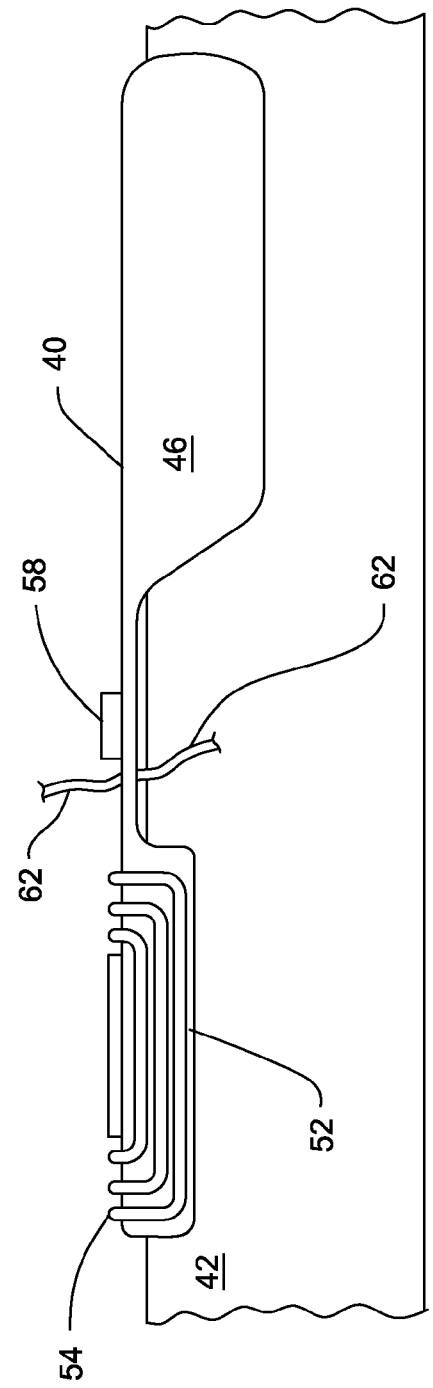

IMPLANTABLE ELECTRODE ARRAY ASSEMBLY WITH EXTRACTION SLEEVE/TETHER

RELATIONSHIP TO EARLIER FILED APPLICATION

This application claims priority from U.S. patent application Ser. No. 12/556,720 filed 10 Sep. 2009. Application Ser. No. 12/556,720 claims priority from U.S. Provisional Patent App. No. 61/096,196 filed 11 Sep. 2008 the contents of which are explicitly incorporated herein by reference.

FIELD OF THE INVENTION

This invention relates generally to a wirelessly powered and controlled electrode array assembly that can be implanted percutaneously. More particularly, this invention relates to such an electrode array assembly with an extraction device that facilitates the post-implantation removal of the array.

BACKGROUND OF THE INVENTION

A number of different medical therapies involve the placement of plural electrodes against tissue located in the body. One such therapy in which positioning of such electrodes is sometimes performed is pain management therapy. Pain management therapy may be necessary when an individual, due to injury or disease, is in a chronic pain state. If little can be done about the source of the pain, an individual may have to live with the chronic feeling of pain. Pain management therapy may also be appropriate when an individual suffers a naturopathic injury or illness. An example of such an injury is when nerve impingement results in nerve damage. A damaged nerve may be the source of pain signals perceived as an ongoing trauma to a region of the body distal to the nerve. A nerve injury may be perceived as a burning sensation.

Pain signals are transferred through the individual's nervous system. More particularly, a pain signal is typically generated by a nerve associated with the tissue that is subject to injury, inflammation or other pain-causing event. The pain signal is transmitted from this local nerve to a network of neurons residing in the spinal cord. The neurons internal to the spinal cord function as the path through which the pain signal is then transmitted to a specific region of the brain. The receipt of the signal by the brain is perceived by the individual as an indication that a particular tissue or organ is in some sort of distress.

Some pain management therapies involve the use of drugs. Certain drugs, for example, interrupt the transmission of the pain signals to the brain. Unfortunately, many of these drugs are globally transmitted through the body via the circulatory system. As a consequence, a drug can produce undesirable systemic effects that may impede the ability of the individual to perform tasks that require constant neural input; driving or machinery operation for example. Some drugs can be administered to a specific site on the body. These drugs only interrupt the transmission of pain signals from a specific location. This type of therapy offers advantages over therapy in which a drug is introduced throughout the body.

To maintain pain relief over a long time period, site-specific drugs are often administrated through portable devices that a patient can wear. A disadvantage of this type of therapy is that an individual may find it difficult to wear this type of device for an extended period of time. It is also known to administer a site-specific drug using a pump implanted in the patient. While these pumps are useful, there are some difficulties associated in refilling them.

An alternative to these therapies is to apply electrical signals to the neural network to counteract the chronic transmission of pain signals. One such therapy involves applying these signals from the epidural space through the dura, the outer covering of the spinal cord, to the nerves forming the dorsal columns of the spinal cord. These columns are located on the dorsal side of the spinal cord. The signals are applied to this portion of the spinal cord because both studies and practice show that, when the nerves in this portion of the spinal cord are stimulated with electrical signals, there is an appreciable masking of the perception of pain.

An advantage of using this electrical stimulus to mask pain signals is that it can be site specific. The control of signals using this type of therapy can often be adjusted so that it does not interfere with the reception or transmission of other neurological signals to or from the brain. Consequently, the masking of the pain signals using this type of therapy does not, for many individuals, impede their abilities to perform daily living tasks.

A number of different electrode array assemblies have been developed that are designed for implantation against the spinal dura. A typical assembly includes multiple individual spaced apart electrodes. Some of these assemblies include a substrate that supports an array of plural rows and columns of individual electrodes. The electrode assembly itself includes a number of longitudinally spaced apart electrodes. Once the electrode assembly is positioned adjacent the dura, current pulses are applied between selected sets of electrodes. These current pulses flow, in part, through the spinal cord. The electrode current flow patterns are experimented with until the individual reports, instead of pain, a more tolerable tingling sensation. This tingling sensation is known as paresthesia.

The Applicants' Assignee's PCT Pat. App. No. PCT/US2009/033769 filed 11 Feb. 2009, the contents of which is explicitly incorporated herein by reference, and are contained in US Pat. Pub. No. US 2011/0077660, also incorporated herein by reference, discloses one electrode array assembly with plural rows and columns of electrodes. The assembly of this invention includes a substrate formed from superelastic material. An advantage of this assembly is that it can be folded into an insertion cannula that is smaller in width than the width of the array itself. The cannula is inserted percutaneously through the skin between vertebra and in the epidural space above the dura. Upon deployment from the cannula, the electrode array assembly unfolds over the dura. An advantage of this invention is that it eliminates the need to make a major incision in the patient and perform a laminectomy or a laminotomy to position the electrode array assembly over the dura.

Electrical stimulation of neural tissue to foster pain relief, sometimes called neuromodulation, is an effective therapy. Nevertheless, like all therapies, success is not guaranteed. Accordingly, presently it is a common practice to initially implant a test electrode array assembly in a patient prior to the implantation of a permanent electrode array assembly. The test electrode array assembly is in the form of a cylinder. After the test assembly is implanted, signals are sourced to the electrodes on the assembly from a source through conductors on the assembly that project out of the patient. The patient's response to the flow of current between the electrodes of the test assembly is monitored, often for several days. Owing to its small size and circular shape, once this analysis is performed, the test assembly can be removed relatively easily.

Ideally, the test results indicate there is a significant likelihood that the patient will benefit from the implantation of a permanent electrode array assembly. However, there is always a chance that the patient did not obtain appreciable relief when the test assembly was activated. This information indicates to the patient and the practitioner that patient may not gain relief if a permanent electrode array assembly is implanted against his/her dura.

The above process reduces the likelihood that an individual is subjected to the expense, and trauma of having a permanent electrode array assembly and complementary pulse generator implanted when there is not a significant likelihood the procedure will offer significant relief.

However, in the event activation of the test array indicates that the patient could benefit from the permanent electrode array, the patient must then be subjected to the trauma of a second procedure to implant the array.

Further, it should be understood that, when the permanent electrode array is implanted, there is no guarantee that its electrodes will be in the same location at which the electrodes of the test assembly were located. Consequently, even though the results with the test array indicated the patient would benefit from such therapy, the results, due to the placement of the permanent array, may yield less than desirable results.

SUMMARY OF THE INVENTION

This invention is directed to a new and useful electrode array assembly adapted for implantation against or within living tissue. The electrode array assembly of this invention includes a carrier on which plural spaced-apart electrodes are arranged in rows and columns. The assembly of this invention also includes an extraction sleeve or tether. A disconnectable connecting member attaches the extraction sleeve/tether to the carrier.

In some versions of this invention, also attached to the carrier is an antenna. The antenna receives signals that supply energy for applying the current to the electrodes. The signals also often include the instructions that indicate between which electrodes the current is to be flowed. In these versions of the invention, a complementary antenna is disposed in the sleeve/tether. In some embodiments of this version of the invention, when the electrode array assembly is initially deployed, the assembly carrier is disposed in the extraction sleeve.

After the electrode assembly of this invention is initially deployed, the sleeve/tether remains attached to the assembly. Often, the sleeve is allowed to extend outside of the body. Signals are applied to the electrodes to cause currents to flow through the tissue located between different combinations of electrodes. These currents are flowed to determine if this activity results in the desired therapeutic effect with, ideally, tolerable side effects. At this time the assembly can be considered to be in a trial state. This trial period can last for several days.

As a result of the trial use of the assembly, it may be determined that the assembly is able to provide the desired therapy with acceptable side effects. In this situation, a severing tool, also part of this invention, is employed to disconnect the extraction tether from the electrode assembly. The sleeve is the removed from the patient. At this time the assembly is considered to be permanently implanted.

During the trial period, it may become apparent that the assembly does not provide the desired end result or that the side effects of the therapy are not tolerable. In these circumstances, the assembly is then removed from the patient. This step is performed by withdrawing the extraction sleeve/tether so as to result in the like withdrawal of the electrode array assembly from the tissue against which it is mounted and out of the patient.

The electrode array assembly of this invention is thus designed to be withdrawn from the patient if it cannot provide a benefit or, if it is able to so provide a benefit, to be left in the patient. Implantation of this assembly thus avoids having to subject an individual to the trauma associated with having to first implant and then remove a trial assembly. Moreover, the same electrode array assembly serves as both the trial and permanent implant. Accordingly, the potential problems with the imprecise positioning of permanent electrode array after the trial array is removed are eliminated.

BRIEF DESCRIPTION OF THE DRAWINGS

The invention is pointed out with particularity in the claims. The above and further features and advantages of this invention are understood from the following Detailed Description in combination with the accompanying drawings in which:

FIG. 1 is a plan view of an electrode array assembly of this invention;

FIG. 2 is a sectional view showing the electrode array disposed over tissue, the specific tissue being the dura of the spinal cord;

FIG. 3 is a longitudinal view of the electrode array assembly of this invention disposed over the spinal dura;

DETAILED DESCRIPTION

Figure 4:
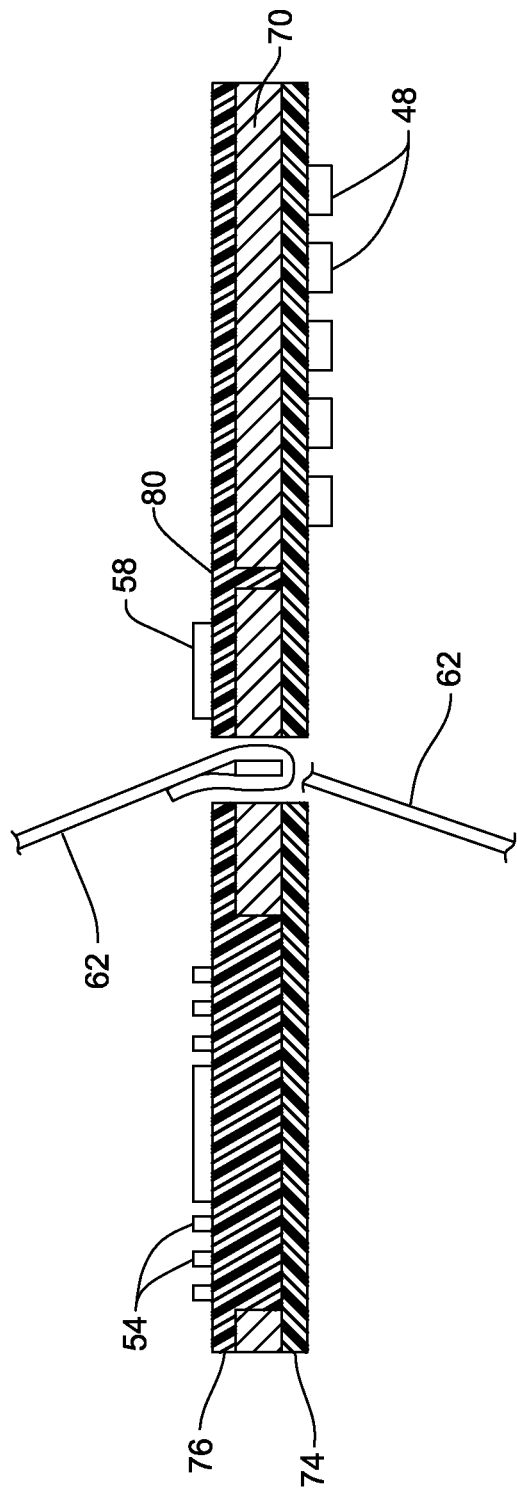
FIG. 4 is a cross sectional view of the electrode array assembly.

FIGS. 1, 2 and 3 illustrate an electrode array assembly 40 constructed in accordance with this invention. Electrode array assembly 40 is designed to be disposed against a section of tissue. In the Figures, the assembly is disposed over the outer dura 42 of the spinal cord 44. Assembly 40 includes a head 46, sometimes called a paddle, that forms one end, the distal end of the assembly. (In this document, "distal" is understood to be toward the most forward edge of assembly head 46; "proximal" is understood to be away from the most forward edge of the assembly head.) A number of electrodes 48 are disposed on the surface of the head 46 and face the dura 42. Electrodes 48 are arranged in rows and columns on head 46. In FIG. 1, a single row of electrodes 48 is shown in phantom because the electrodes are on the surface of assembly head 46 opposite the surface depicted in the Figure.

Assembly head 46 tapers inwardly to define a neck 50. Neck 50 thus has a width less than that of head 46. Continuing proximally, the assembly neck 50 tapers outwardly to define a foot 52. In the illustrated version of the invention, assembly foot 52 has a width greater than that of head 42. In alternative versions of the invention, foot 52 may have a width less than or equal to that of the head 42. Foot 52 may even have a width equal to or less than assembly neck 50.

An antenna 54 is disposed on assembly foot 52. Antenna 54 receives signals from an implantable generator disposed in the body of the patient at some location spaced from assembly 40. Electrode array assembly 40 includes a control circuit 58, represented by a block on neck 50, that receives the signals developed across antenna 54. Control circuit 58 stores the energy contained in these signals. The control circuit 58 also demodulates the signals to extract control signals. Based on the instructions contained within the control signals, control circuit 58 causes current to flow between specific combinations of the electrodes. This current flows through the tissue between the electrodes so as to have a therapeutic effect on the patient.

The Applicants' Assignee's PCT Pub No. WO 2008/080073 A2, the contents of which are incorporated herein by reference, describe how energy from a device worn by the patient is transmitted to the implantable pulse generator (not illustrated) and the implantable pulse generator transmits these signals to the electrode array assembly. This document also describes how the control circuit integral with the electrode array assembly: saves the energy contained in the signals; extracts the commands based on the signals and; based on the commands, causes current flow between selected electrodes 48. Again, it should be understood that the means by which signals are processed by electrode array assembly 40 are not relevant to this invention.

Figure 6:
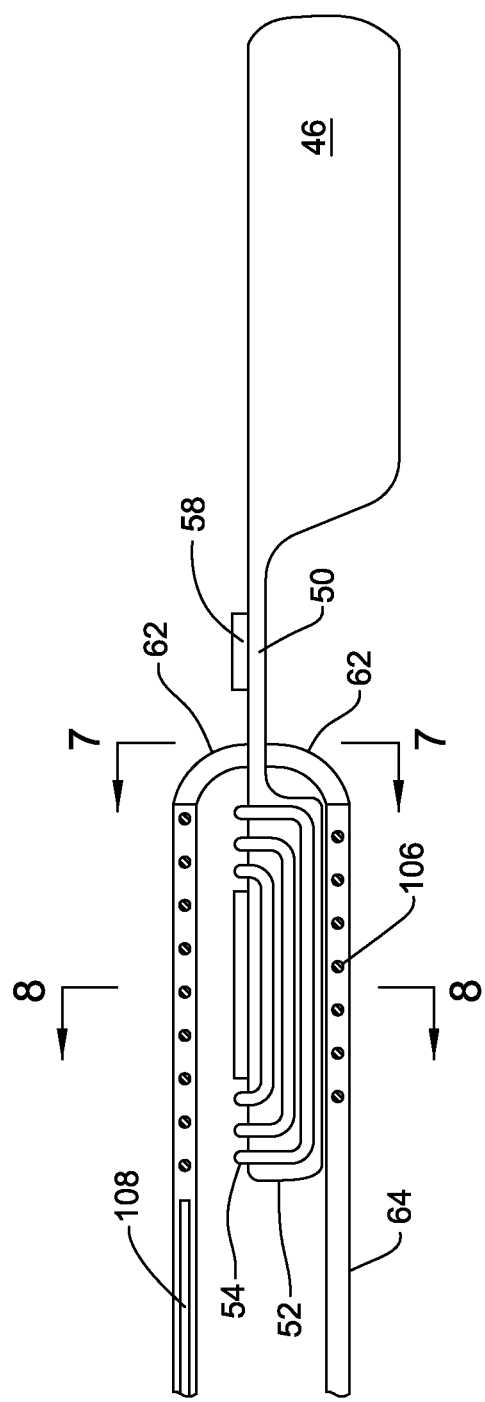
FIG. 6 is a side and partial cross sectional view of the electrode array assembly disposed in an extraction sleeve.

Also part of electrode array assembly 40 are one or more extraction webs 62. Webs 62 hold the assembly to an extraction sleeve 64 (FIG. 6). Once the assembly is so deployed 40, signals are supplied to the antenna from an antenna (coil 106) within the extraction sleeve 64. If, post deployment of the assembly 40, it becomes necessary to extract the assembly, the assembly is removed by pulling on the extraction sleeve 64. If such removal is not required, sleeve 64 is severed from webs 62 and removed. This leaves the electrode array assembly 40 in a fully deployed state.

Figure 5:
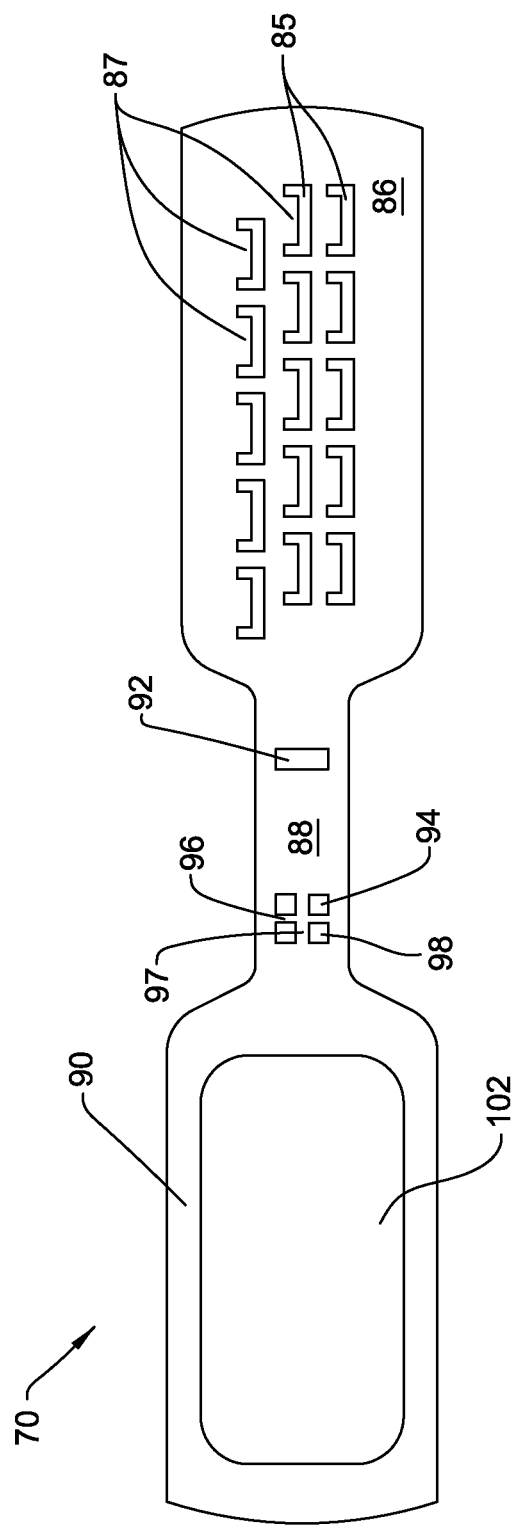
FIG. 5 is a plan view of the carrier on which the electrode array assembly is formed.

As seen by reference to FIGS. 4 and 5, the electrode array assembly 40 of this invention includes a carrier 70. Carrier 70 is formed from a superelastic material. This is a material that, after being subjected to appreciable bending, rolling or other deformation, returns to its initial state. One such superelastic material is a nickel-titanium alloy such as the alloy marketed as Nitinol.

In many embodiments of the invention, as part of the process of fabricating the assembly, carrier 70 is given a shape to facilitate conformance of the assembly to the tissue against which the assembly is to be disposed. Thus, in a version of the assembly intended for implanting against the spinal cord dura 42, carrier 70 is curved to have arc that is perpendicular to the longitudinal axis of the assembly 40. Not all sections of the carrier may be so curved. For example, in the above described version of the invention only the head- and foot-defining portions of the carrier may be so curved; neck 50 is not curved.

Bottom and top insulating layers 74 and 76, respectively, are disposed over carrier 70. Insulating layers 74 and 76 are formed from electrically insulating material. For example, in some versions of the invention a polyxylene polymer film, such as parylene-C which is available from Specialty Coating Systems, Inc., functions as the material from which the insulating layers are formed. Electrodes 48 are over the bottom insulating layer 74, the layer directed towards the dura 42. Antenna 54 and the assembly the control circuit 58 are disposed on top insulating layer 76. (In the Figures, the heights of the electrodes 48, antenna 54 and control circuit 58 are exaggerated for purposes of illustration.)

Conductors 78 and 82 serve as the components over which connections are established between the electrodes 48 and the control circuit 58. Conductors 78 (only two shown in FIG. 1) are connected to the control circuit 58 and are located on the top insulating layer 76. Conductors 82 (only two shown in phantom in FIG. 1) are disposed on the bottom insulating layer 74 and are connected to the electrodes 48. Conductors 78 and 82 are connected together by vias 80 (one shown in FIG. 4) that extend from bottom insulating layer 74, through the carrier 70 to the top insulating layer 76.

The Applicants' Assignee's U.S. patent application Ser. No. 12/475,920, METHOD OF ASSEMBLING AN ELECTRODE ARRAY THAT INCLUDES A PLASTICALLY DEFORMABLE CARRIER, filed 1 Jun. 2009, now U.S. Pat. Pub. No. US 2009/0293270, the contents of which is incorporated herein by reference, discloses one means by which bottom insulating layer 74, electrodes 48 and conductors 82 are fabricated on a first side of carrier 70. Once these components are so assembled on the carrier, using the same method of the incorporated by reference U.S. Pat. Pub. No. US 2009/0293270, the carrier 70 is inverted. Top insulating layer 76, antenna 54 and conductors 78 are fabricated on the surface of the carrier 70 opposite the surface on which the electrodes 48 and conductors 82 are fabricated. During the process steps in which antenna 54 and conductors 78 are formed on the assembly, vias 80 are formed to extend through between the conductors 78 and 82 and therefore through the carrier 70. Again, it should be understood that, unless otherwise called out, the process by which electrode array assembly 40 of this invention is manufactured is not material to the invention.

FIG. 5 illustrates the structure of carrier 70 in more detail. Prior to any bending operation, carrier 70 has a planar shape. The carrier 70 is formed to define a head 86, a neck 88 and a foot 90. Carrier head 86, neck 88 and foot 90 have outer perimeters that generally correspond to the outer perimeters of assembly head 46, neck 50 and foot 54, respectively. The width and length of the assembly 40 is slightly greater then that of the carrier 70. This difference is due to the fact that, while not completely illustrated, in the completed assembly 40, a layer of insulating material is disposed around the edge surfaces of the carrier 70.

Carrier head 86 is formed with a number of tabs 87. Tabs 87 are located internal to the outer perimeter of the carrier 70. The tabs 87 are defined by three sided slots 85. Tabs 87 are arranged in rows and columns on the interior of the carrier head 86. As described in the incorporated by reference U.S. Pat. App. Ser. No. 61/034,367, the contents of which are contained in US Pat. Pub. Ser. No. 2011/0077660, tabs 87 function as the sections of the carrier head 86 on which the electrodes 48 are formed.

In FIG. 1, electrodes 48 are seen disposed on tabs 49 integral with assembly head 46. Carrier tabs 87 and the insulating material disposed over and under the carrier tabs 87 form the assembly tabs 49. When the electrode assembly head 46 is rolled or folded, tabs 49 and by extension, the electrodes 48 thereon, are not rolled or folded to the extent the surrounding sections of the electrode array assembly head is so rolled or folded. For reasons of ease of illustration, the assembly tabs 49 are not seen in any drawings other than FIG. 1.

Carrier 70 is further formed to have an opening 92 in the neck 88 that is proximal to carrier head 86. Opening 92 is the opening through which vias 80 extend through the carrier 70.

Carrier neck 88 is also formed to have additional openings 94 and 98 that, while separate, are spaced relatively close to each other. Each of openings 92, 94 and 98 has a longitudinal axis that extends perpendicular to the longitudinal axis of the carrier 70. Openings 94 and 98 are closer to the carrier foot 90 than to opening 92. Openings 94 and 98 define a bar 96 between the openings. Bar 96, which is part of the carrier 70, has a longitudinal axis that extends perpendicular to the longitudinal axis of the carrier. A bridge 97, also part of the carrier 70, bisects openings 94 and 98 and the bar 96. Bridge 97 functions as the portion of the carrier 70 over which conductors 78 extend over the assembly neck 50 from the antenna 54 to control circuit 58.

Carrier foot 90 is formed to have an opening 102. Opening 102 defines the area on the top insulating layer 76 over which antenna 54 is disposed. Opening 102 is present to prevent the electromagnetic energy shielding tendencies of the metal-formed carrier 70 from interfering with the receipt or transmission of signals over antenna 54. In FIG. 5, opening 102 is shown has having a generally rectangular shape and being wholly enclosed by the carrier 70. It should be understood that the shape of the opening and whether or not it is wholly surrounded or open may vary in other versions of this invention.

In FIG. 4, the material forming top insulating layer 76 is shown in openings 92 and 102. While not illustrated, it should likewise be understood that at least the edges of the carrier that define slots 85 and openings 94 and 98 are likewise covered with insulating material.

Figure 7:
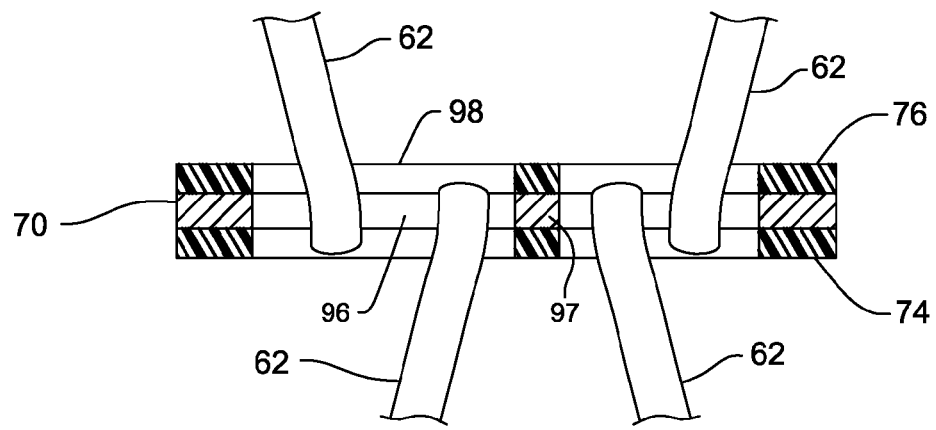
FIG. 7 is a lateral cross sectional view of the electrode array assembly taken along line 7-7 of FIG. 6.
Figure 8:
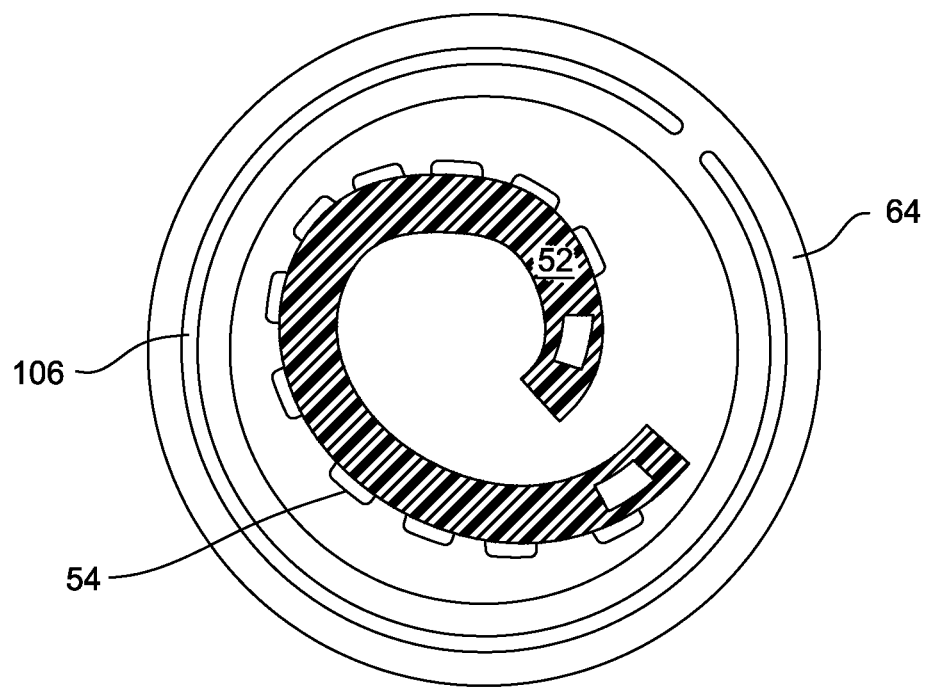
FIG. 8 is a lateral cross sectional view of the electrode array assembly taken along line 8-8 of FIG. 6.

The extraction sleeve 64, now described by reference to FIGS. 6, 7 and 8, is formed from non-conductive, material that is generally tubularly shaped. For example, the extraction sleeve 64 may be formed from a polymer tube that has an outer diameter of between 1.5 and 5.0 mm and a wall thickness of between 0.05 and 0.5 mm. Extraction sleeve 64 has an open distal end, (end not identified). Extraction webs 62 are formed integrally with the extraction sleeve 64 and extend forward from the distal end face of the sleeve.

Immediately proximal to the distal end of the sleeve 64 a coil 106 is disposed in the extraction sleeve. In FIGS. 6 and 8, coil 106 is depicted as a wire wrapped as a helix wherein the individual turns are spaced apart from each other. At least one conductor 108 extends proximally through the sleeve 64 from coil 86. In some versions of the invention, extraction sleeve 64 is constructed by molding the sleeve around coil 106 and conductor 108. Alternatively, sleeve 64 is formed from inner and outer tubes of material. Prior to the bonding of the two tubes of material to form sleeve 64, coil 106 and conductor 108 are formed over the inner sleeve or inside the inner wall of the outer sleeve. As a consequence of the tube bonding process, coil 106 and conductor 108 are embedded on the extraction sleeve 64.

After electrode array assembly 40 of this invention is assembled, the assembly foot 52 is rolled or folded and inserted in the distal end of extraction sleeve 64. The forward ends, the distal ends, of webs 62 are looped around carrier bar 96. In the depicted version of the invention, two webs 62 are looped around the carrier bar 96 from the top of assembly 40; two webs 62 are looped around the carrier bar from the bottom of the assembly 40. The free end of each web 62 is attached to a more proximal portion of the web 62. An adhesive may be used to facilitate this attachment. As a consequence of the seating of assembly 52 in the distal end section of extraction sleeve 64, assembly antenna 54 is disposed within the space enclosed by sleeve coil 106 as seen by FIG. 8.

Figure 9:
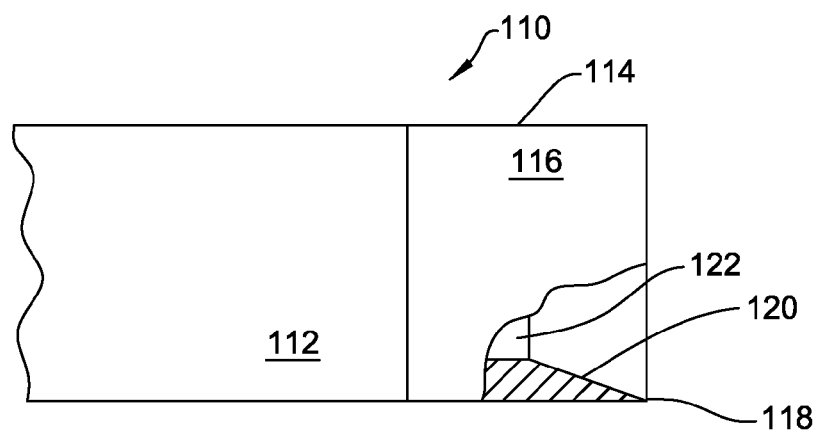
FIG. 9 is a side and partial cross sectional view of the severing tube of this invention.

A severing tube 110, seen in FIG. 9, is used to disconnect the electrode array assembly 40 from the extraction sleeve 64. Severing tube 110 includes a tubular-shaped body 112 formed from flexible material. One such material from which tube body can be formed is Nitinol. Tube body 112 has an outer diameter that allows the tube 110 to be slid in extraction sleeve 64.

Severing tube 110 has a ring-shaped head 114 attached to the distal end of tube body 112 that forms the distal most end of the tube 110. Head 114 is formed from metal such as medical grade stainless steel. Head 114, like body 112, is dimensioned to slip fit within extraction sleeve 64. In the illustrated version of the invention, head 114 has an outer circumferential surface 116 with the same outer diameter as body 112. At the most distal end of the head 114 there is an inner circumferential surface 120. Surface 120 starts at the most forward end of outer surface 116 and tapers inwardly from the distal end, the open end, of head 114. Thus, severing tube head 114 is shaped to define between outer circumferential surface 116 and inner circumferential surface 120 a cutting edge 118. Cutting edge 118 is the most forward circumferential face of head 114 and, by extension, severing tube 110.

In the illustrated version of the invention, inner circumferential surface 120 does not extend the whole of the length of head 114. Instead, surface 120 extends a distance equal to approximately 20 to 75% of the length of head 114. Rearward of surface 120, head 114 is shaped to have a second inner circumferential surface, surface 122 that has constant diameter. In some versions of the invention, surface 120 has a diameter equal to the diameter of the adjacent bore-defining inner surface of tube body 112.

Figure 11:
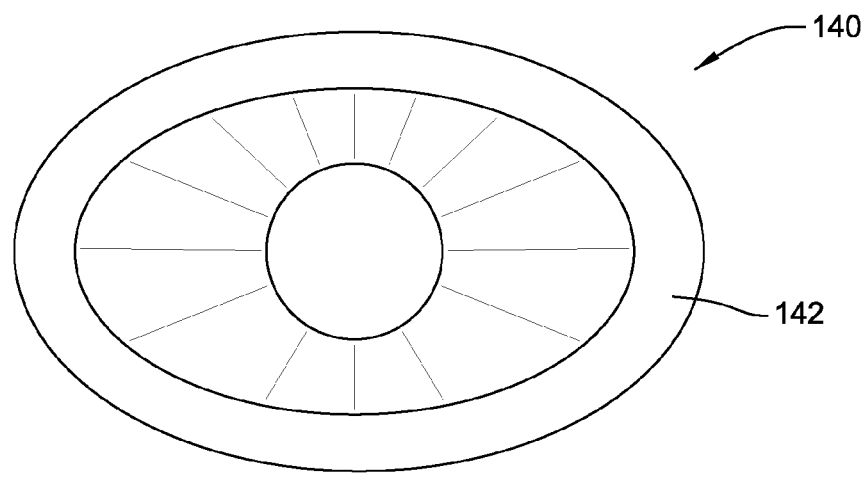
FIG. 11 is a front plan view of the front end of the head of the extraction tube.
Figure 10:
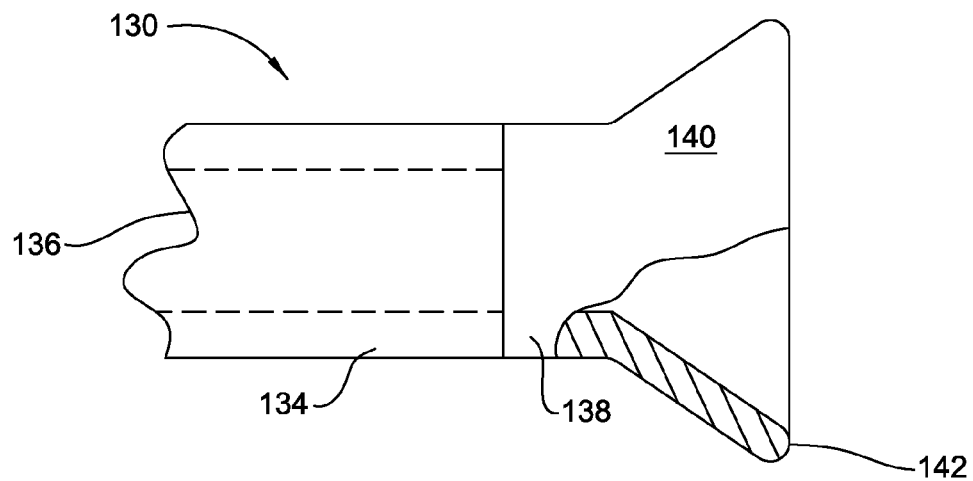
FIG. 10 is a side and partial cross sectional view of the extraction tube.

In the event it is necessary to remove the electrode array assembly 40 from the patient, an extraction tube 130, now described by reference to FIGS. 10 and 11, is employed to so remove the assembly. Extraction tube 130 has a tube body 134 formed from the same material from which severing tube body 112 is formed. Tube body 134 is formed to have an inner lumen 136 (shown in phantom) with a diameter that allows the extraction sleeve 64, with assembly foot 52 contained therein, to be drawn into the body 134.

Extraction tube 130 has a neck 138 and a head 140 formed as a single unit, that is disposed over the distal end of tube body 134. Neck 138 and head 140 may be formed from metal or from a plastic that is more rigid from which tube body 134 is formed. Neck 138 is generally ring shaped and has inner and outer diameters that are generally identical to the inner and outer diameter of extraction tube body 134.

Head 140 generally is generally horn shaped. That is, both the inner and outer walls of the head 140 flare outwardly from the distal end of the neck 138. In the illustrated version of the invention, head 140 has in a plane perpendicular to the longitudinal axis of the neck 138 and head 140 an elliptical cross sectional profile. That is, head flares outwardly more along a first axis perpendicular to the longitudinal axis than along a second axis this is perpendicular to both the longitudinal and the first axis. Head 140 is further formed so as to have rounded edge 142 between the inner and outer circumferential surfaces. Rounded edge 142 thus functions as the most forward face of head 140 and, therefore, of extraction tube 130.

As mentioned above, once electrode array assembly 40 is fabricated, foot 52 is rolled or fabricated so the foot can be inserted in the open distal end of the extraction sleeve 64. In FIG. 8, foot 52 is shown as being in a rolled state. Webs 62 are looped around carrier bar 62 and their ends attached to their more proximal portions.

Figure 12:
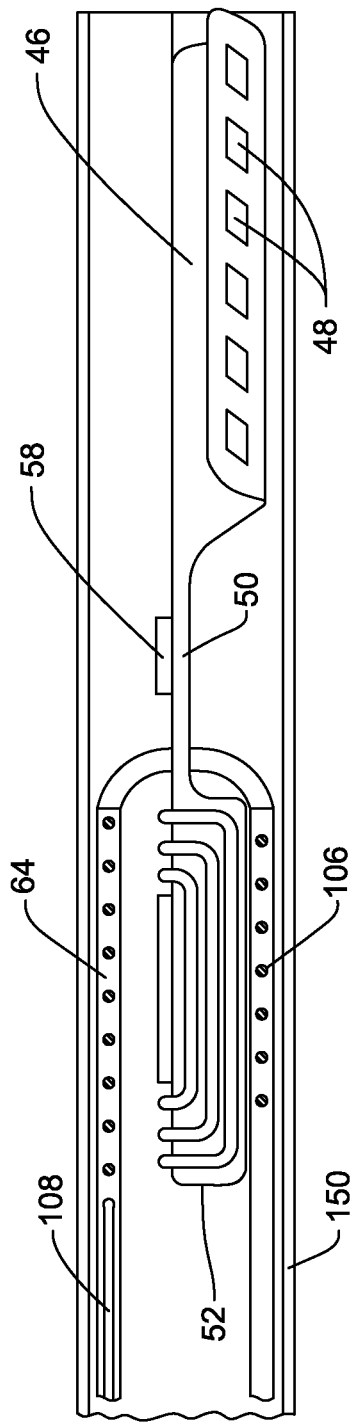
FIG. 12 is a partial cross sectional view of the electrode array assembly and extraction sleeve positioned in an inner or deployment cannula.

The electrode array assembly-and-extraction sleeve assembly is then placed in an inner cannula, sometimes referred to as a deployment cannula 150, seen in FIG. 12. Deployment cannula 150 is placed in an outer cannula sometimes referred to as an access cannula (access cannula not illustrated). Also, prior to insertion of the deployment cannula 150 with the assembly contained therein, a flexible stylet (not illustrated) may be fed through the cannulae and the extraction sleeve. The distal end of the stylet abuts the proximal end of the electrode array assembly foot 52.

Electrode array assembly 40 is deployed by first positioning the access cannula in close proximity to the tissue over the tissue over with which electrode array assembly is to be disposed. The deployment cannula 150, with the electrode array assembly-and-extraction sleeve assembly contained therein, is pushed forward over the target tissue. During advancement of the deployment cannula 150, the deployment cannula 150 may be rotated relative to the access cannula.

Once the deployment cannula 150 is in position, the deployment cannula 150 is retracted back into the access cannula. At the time of the retraction of the deployment cannula, the stylet holds the electrode array assembly-and-extraction sleeve assembly so that this assembly does not retract back into the access cannula with the deployment cannula 10. A more detailed understanding of this process may be found in the incorporated by reference PCT Pat. App. No. PCT/US2009/033769/US Pat. Pub. No. US 2011/0077660.

Figure 13:
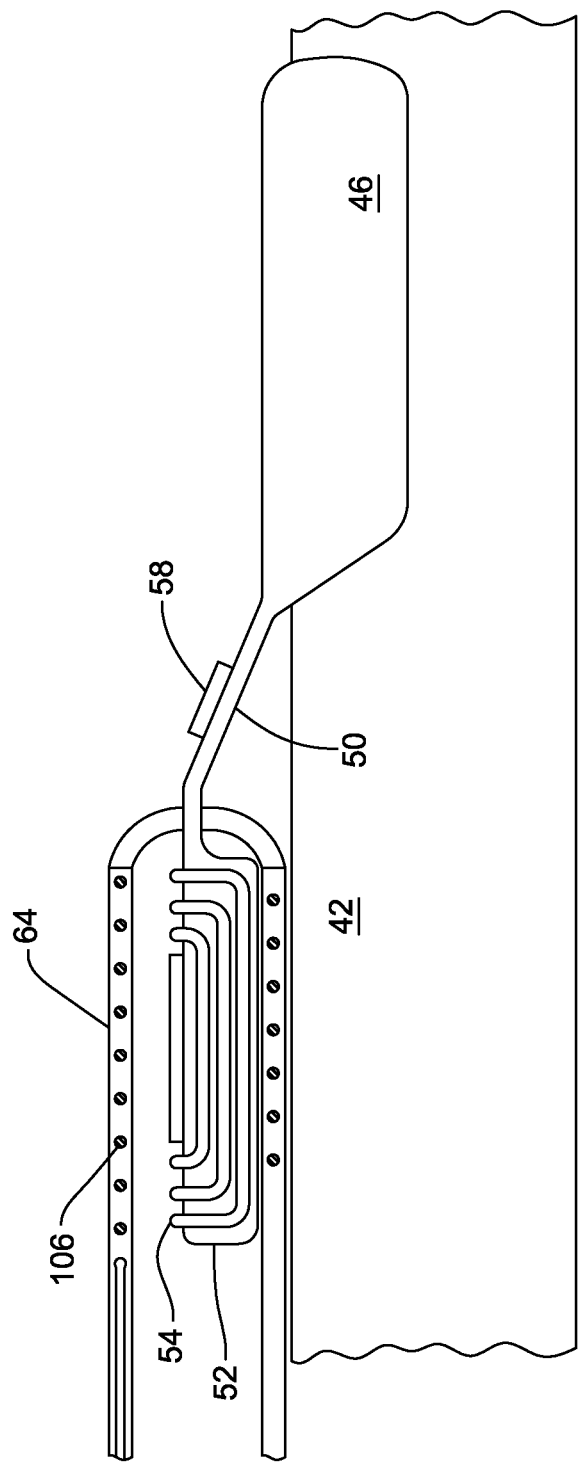
FIG. 13 is a side and partial cross sectional view of the electrode array assembly deployed over the spinal dura when the assembly foot is still disposed in the extraction sleeve.

As a consequence of the retraction of deployment cannula 150 and the superelasticity of the assembly carrier 70, as depicted in FIG. 13, the assembly head 46 deploys over the surface of the tissue over which the head is to be positioned. Assembly foot 52 remains contained in extraction sleeve 64. Extraction sleeve 64 thus rests on the surface of the tissue adjacent the tissue over which the assembly head 46 is deployed. In FIG. 13, the height of the extraction sleeve above the tissue and assembly head 46 is exaggerated for purposes of illustration.

Figures 14, 14A:
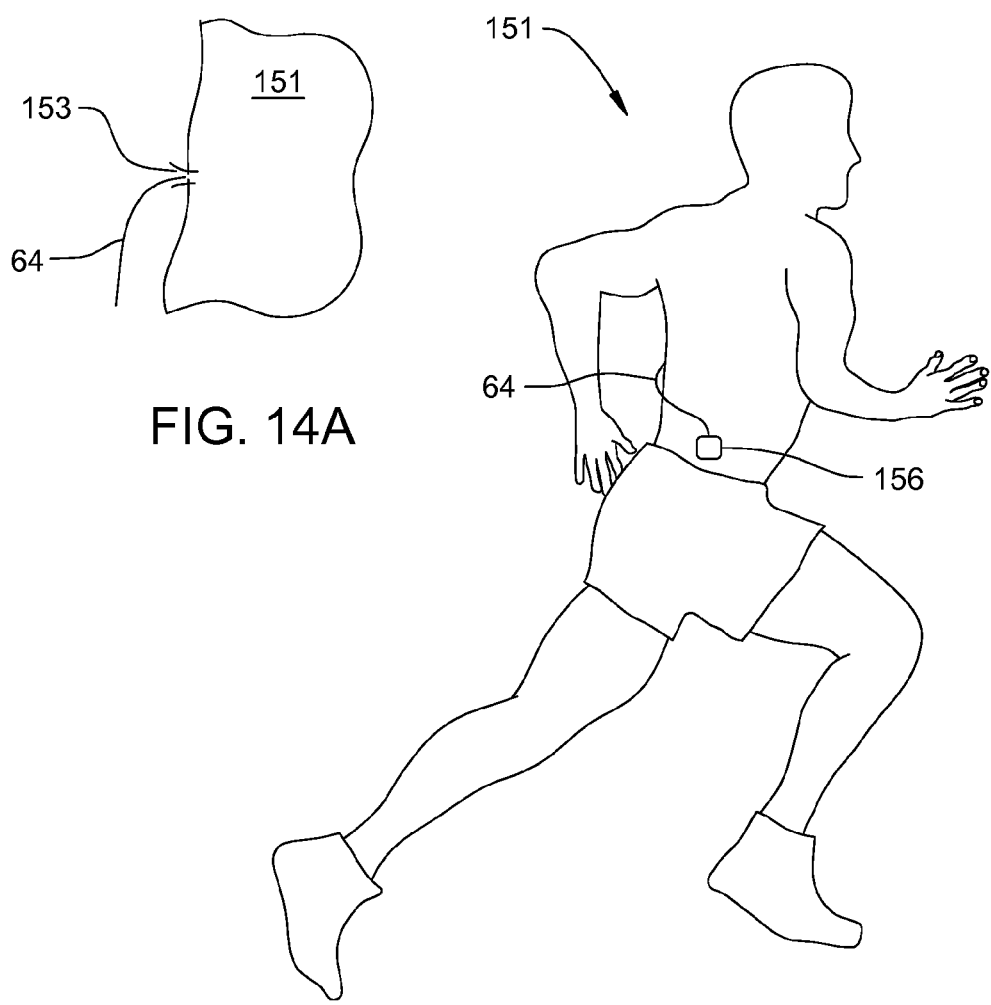
FIG. 14 is a diagrammatic view of how the extraction sleeve extends out of the body of the patient and the externally worn power and control unit used to actuate the electrode array assembly.
FIG. 14A is an enlarged view of where the extraction sleeve is extends out of the portal formed in the patient.

Owing to its length, after withdrawal of the access and deployment cannulae, the proximal end of the extraction sleeve 64 extends out of the body 151 as seen in FIGS. 14 and 14A. More particularly, the extraction sleeve 64 extends out of the portal 153 formed in the body 151 through which the cannulae was introduced into the body. Conductor 108 is connected to a power and control unit 156 adapted to be worn externally by the individual in whom the electrode array assembly 40 is implanted (actual connection of conductor 108 not shown).

Power and control unit 156 is programmed to determine if assembly 40 can provide the desired therapeutic effect. Specifically, power and control unit 156 is programmed to output signals containing instructions indicating between which sets of electrodes currents are to be flowed. These signals are generated by unit 156 and output over conductor 108 to coil 106. Coil 106 functions as antenna that broadcasts the signals to the adjacent electrode array assembly antenna 54. Control circuit 58 both extracts the power from the signals received by antenna 54 and decodes the instructions contained in the signals. Based on the decoded instructions, control circuit 58 causes current to flow between the specified sets of electrodes 48.

The current flow between the electrodes 48 flows through the tissue underlying the electrodes. The patient is monitored to determine if this current flow has the desired therapeutic effect and results in tolerable side effects. During this evaluation process, unit 156 typically is reprogrammed to output instructions that cause the currents to be flowed through different sets of electrodes. This resetting of the current flow patterns through the patient's tissue is performed to determine which current flow results in an optimal combination of desirable benefits and acceptable side effects.

Figure 15:
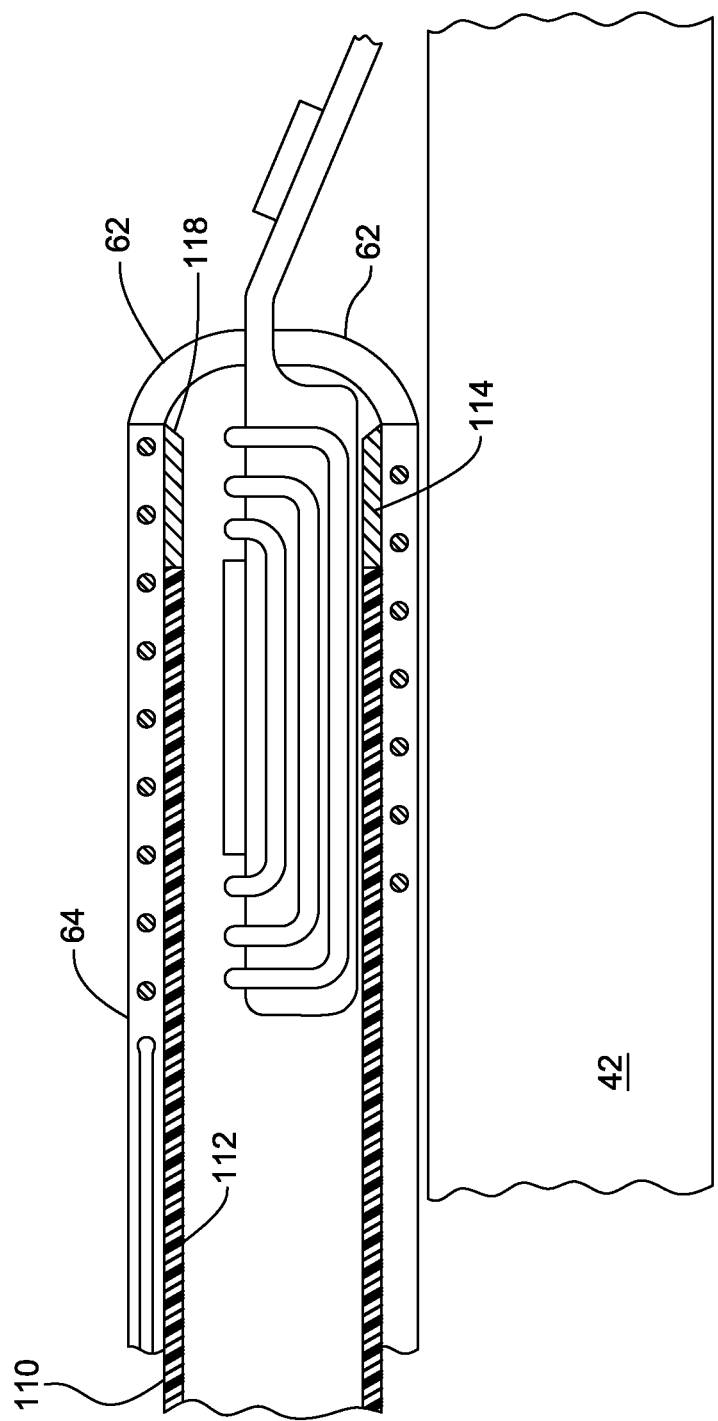
FIG. 15 is a side and partial cross sectional view of how the severing tube is employed to sever the extraction sleeve from the deployed electrode array assembly.

Ideally, during this evaluation process, it becomes apparent that the electrode array assembly 40 provides the desired benefits with, at the most, acceptable side effects. In this situation, the extraction sleeve 64 is removed. The removal is performed by sliding severing tube 110 down the center lumen of the extraction sleeve 64 as seen in FIG. 15. When the tube head 114 approaches the assembly 40, the assembly foot 52 slides up against the inner circumferential surface 120 of the head 114. The assembly foot 52 thus becomes encased in the tube body 112 and head 114. Severing tube 110 is continued to be pressed forward so that head cutting edge 118 presses against and cuts webs 62.

During the process of pressing severing tube 110 against webs 62, it may be necessary to apply a restraining force to the extraction sleeve 64. This force prevents sleeve 64 and attached electrode array assembly 40 from moving forward when the severing tube head 114 is pressed against webs 62. A flexible stylet threaded down the extraction sleeve 64 so as to abut the electrode array assembly 40 can provide this force.

Figure 21B:
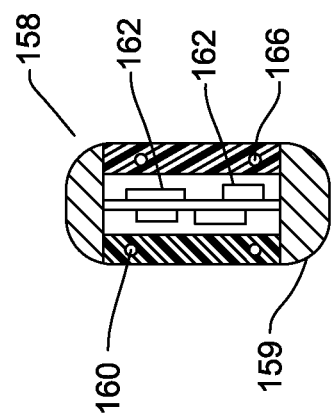
FIGS. 21A and 21B are plan and cross sectional views of an implantable pulse generator that can be used to transmit signals to the electrode array assembly of this invention once the extraction tether or sleeve is disconnected.
Figure 21A:
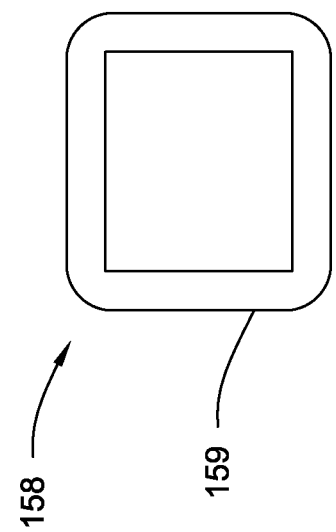

Once the webs 62 are cut, extraction sleeve 64, and severing tube 110 encased therein, are withdrawn from the patient. Owing to the superelastic nature of assembly carrier 70, assembly foot 52 unrolls or unfolds to extend over the tissue adjacent the tissue over which the assembly head 46 is deployed as seen in FIG. 3. Electrode array assembly 40 can now be considered permanently implanted in the patient. Once this procedure is performed, a pulse generator 158, seen in FIGS. 21A and 21B, is implanted in the patient. As described in the incorporated herein by reference PCT Pub. No. WO 2008/080073, this pulse generator 158 includes a housing 159 in which two antennae 160 and 166 are embedded. Antenna 160 is used to receive signals from a source external to the patient. A circuit internal to housing 159, represented by components 162, converts these signals into a form in which they can be used by the electrode array assembly 40. The converted signals are applied to antenna 166.

Antenna 166 wirelessly transmits signals to array antenna 52. As before, control circuit 58 harvests the power from these signals and decodes the signals. Based on the decoded instructions, control circuit 58 causes the inter-electrode current flow necessary to have the desired therapeutic effect. The exact structure of this implantable pulse generator is not part of the current invention. As described in the incorporated by reference US Pat. Pub. No. US 2011/0077660, array antenna 40 is also capable of transmitting signals through coil 44 back to the pulse generator 158.

There are situations though during the evaluation process in which it is determined that the current flows through the patient's tissue does not have the desired benefit or the side effects of such current flow are not tolerable. This determination may be made even though by reprogramming power and control unit 156, currents were flowed through different sets of electrodes 48 and, therefore by extension, through different sections of tissue underlying the assembly 40.

Figure 16:
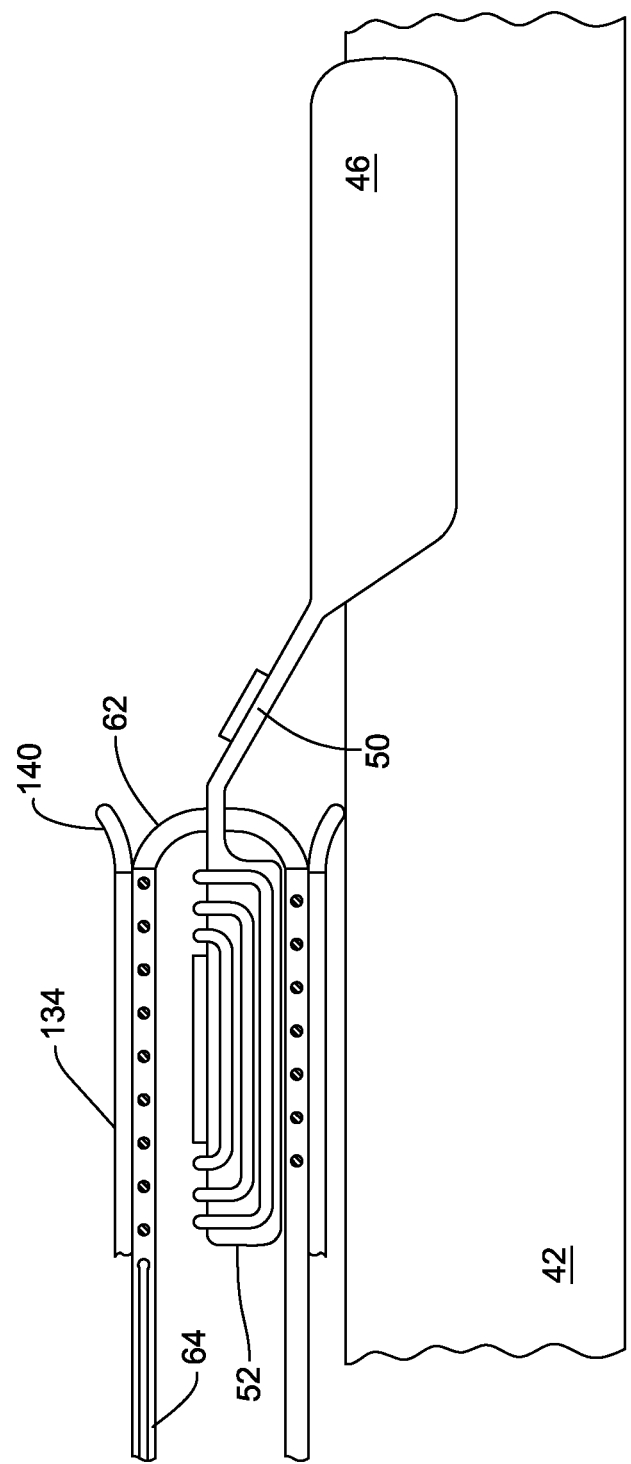
FIG. 16 is a side and partial cross sectional view of how the extraction tube is used to guide the removal the electrode array assembly and the extraction sleeve.

In this event, there is no reason to leave the electrode array assembly 40 in the patient. Accordingly, the extraction tube 130 is inserted in the portal around the extraction sleeve 64 and feed forward to the electrode array assembly. As a consequence of the of the extraction tube 130 sliding over the distal end of the extraction sleeve 64, the assembly foot 52 lodges in the distal end of the tube body 134 and tube head 140 as seen in FIG. 16. Owing to the relative dimensioning of the extraction sleeve 64 as well as the extension tied to it and the extraction tube, at this time the extraction sleeve extends out of the proximal end of extraction tube body 132. The proximal end of the extraction sleeve 64 is pulled on to draw the electrode array assembly neck 50 and then head 46 into the tube body 134. As the electrode array assembly head moves into tube 130, the outer portions of the assembly head 46 move against the wide to narrow tapered surface of tube head 140. This movement of the assembly head 46 against tube head 134 folds the outer portions of the assembly head inwardly. Once folded, these portions of the assembly head 46 are able to slide within the lumen 136 of the tube body 134.

Once the electrode array assembly 40 is disposed within the extraction tube, the tube 130, with assembly 40 and sleeve 64 contained therein, is withdrawn from the patient. The withdrawal of the extraction tube 130 thus removes the electrode array assembly 40 from the patient.

Electrode array assembly 40 and the complementary components of this invention are designed so that the assembly 40 serves as its own evaluation assembly. During the evaluation period, the energy and power containing signals are transmitted wirelessly to the assembly 40 from the external power and control unit 156 through extraction sleeve 64. This eliminates the need to initially implant a pulse generator in a patient before it has been determined that the assembly 40 provides a beneficial effect.

Ideally, once implanted, it is determined in the evaluation procedure that the assembly provides the desired therapeutic effects. In this situation, the patient is subjected to a minor procedure to disconnect the extraction sleeve 64 from the assembly 40 and withdraw the sleeve. The need to subject the patient to a second more complicated medical procedure to withdraw a test electrode array and then install the permanent array is eliminated.

Further, since electrode array assembly 40 serves as its own test array, the possibility that the replacement of a test array with a permanent electrode array results in the mispositioning of the permanent array is likewise eliminated.

However, there will be instances in which during the evaluation period it is determined that the electrode array assembly 40 is not able to provide the patient with the desired therapeutic effects or the side effects are not tolerable. When this situation occurs, the extraction sleeve 64 and extraction tube 130 are collectively employed to withdraw, extract, the assembly 40 from the patient. The assembly is withdrawn through the previously formed portal in the patient. Again, this minimizes the trauma to which the patient is subjected.

It should be appreciated that the foregoing is directed to one specific version of the invention. Certain features of the invention may differ from what has been described.

For example, means other than the described web-around-bar arrangement may be used to hold the electrode array assembly 40 within extraction sleeve 64. In some versions of the invention, webs 62 maybe adhesively or heat bond secured to one or more of the exposed surfaces of the electrode array assembly.

Figure 17:
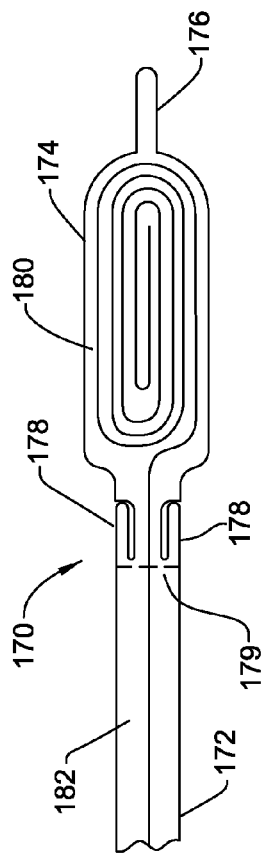
FIG. 17 is a top plan view of a second extraction tether of this invention.
Figure 18:
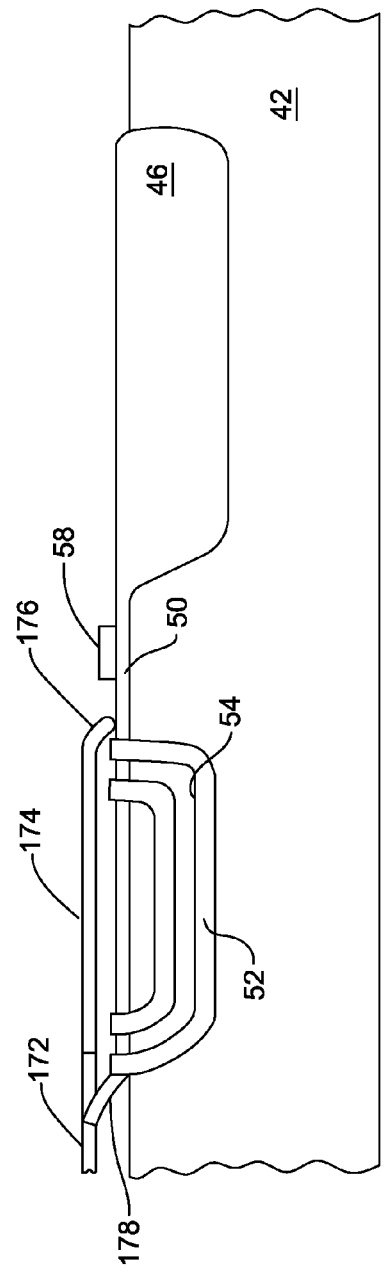
FIG. 18 is a side view of the electrode array assembly deployed over tissue showing the extraction tether of FIG. 17 attached to the assembly.

Alternatively, a structural device other than a sleeve may serve as the extraction device connected to the electrode array assembly to which the withdrawal force is applied. FIGS. 17 and 18 illustrate how a planar strip of plastic functions as the extraction tether 170. In this version of the invention, extraction tether 170 has a relatively narrow body 172. A head 174 with a width greater than body 172 is located at the distal end of the body 172. A nose 176 with a width less than that of head 174 extends forward from the head. Nose 176 thus forms the most distal end of extraction tether 170.

In this version of the invention, tether 170 is positioned so that head 174 is disposed over assembly foot 52. Nose 176 is secured to the assembly 40 forward of antenna 54. In some versions of the invention, the most distal end of tether nose 176 is looped around carrier bar 96 and secured to a more proximal section of the nose 176. Alternatively, the nose 176 is adhesively secured to the electrode array assembly 40.

Tether body 172 has two arms 178. Each arm 178 is in the form of a section of the body 172 that is separated from the adjacent section of the body a small slot formed in the body (slot not identified). The arms 178 are located along the opposed outer longitudinally extending sides of the body 172. Arms 178 are located immediately proximal to tether head 174. Each arm 178 is a three-sided structure. The arms 178 thus extend from fold line 179. Each arm 178 bends down from the adjacent section of the tether body 172.

The forward end, the distal end, of each tether arm 178 is attached to the proximal end of the associated electrode array assembly foot 52. Just as an adhesive is used to secure tether nose 176 to the electrode array assembly 40, an adhesive may be used to secure the arms to the assembly.

An antenna 180 is disposed in tether head 174. In the illustrated version of the invention, the antenna 184 is in the form of a spiral wrapped wire. At least one conductor 182 extends proximally from antenna 180 through tether body 172.

When tether 170 is attached to electrode array assembly, tether head 174 is disposed over assembly foot 52. Tether nose 176 and arms 178 connect tether 170 to assembly 40 at opposed ends of the assembly foot 52. Tether antenna 180 overlaps assembly antenna 54.

The above described version of the invention works in the same general manner in which the first described version functions. The electrode array assembly-and-tether assembly is implanted at the location where it is believed current flow through the tissue will have the desired therapeutic effect. Signals are transferred between the tether antenna 180 and the underlying assembly antenna 54.

If, during the evaluation period, it is determined that the assembly 40 provides the desired therapeutic effect, tether 170 is removed. A severing tube similar to the previously described severing tube 110 may be used to perform this function. The severing tool of this version of the invention may have small inner and outer diameters than tool 110. This is because the width of the tether body 172 is less than the width of the assembly foot 52 even when the foot is folded or rolled. As the severing tool approaches the distal end of the tether 170 the tether head 174 folds into the severing tool. By pushing forward on the severing tube, the tube head first cuts tether arms 178 and then tether nose 176 so as to separate extraction tether 170 from electrode array assembly 40.

If it is necessary to remove the electrode array assembly, an extraction tube similar to the previously described extraction tube 130 is employed. Since the extraction tether 170 has an on overall circumference that is less than the previously described extraction sleeve, the extraction tube of this invention may be of smaller diameter than the previously described extraction tube 130. The extraction tube is fed over the extraction tether body 172 until the head of the tube is close to tether head 174. At this time force is applied to the proximal end of the extraction tether body 172 to pull the tether 170 into the extraction tube. Since, the tether nose 176 and arms 178 are connected to the electrode array assembly 40, the retraction of the tether 170 into the extraction tube results in a like retraction of the electrode array assembly 40. As part of this process, first the extraction tether arms 178 and then the head 176 pull the electrode array assembly 40 into the head of the extraction tube. Once the electrode array assembly 40 is disposed in the extraction tube, the tube is withdrawn from the patient to complete the extraction process.

Figure 19:
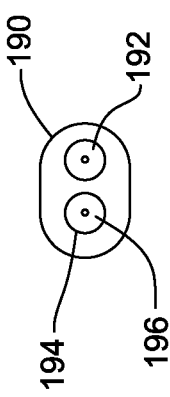
FIG. 19 is a front plan view of a third extraction tether of this invention.
Figure 20:
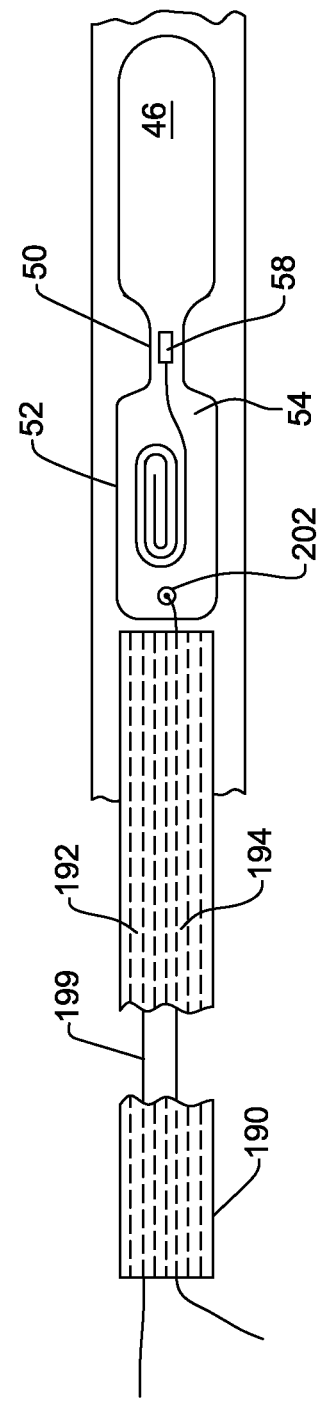
FIG. 20 is a top view of the electrode array assembly deployed over tissue showing the extraction tether of FIG. 19 attached to the assembly.

FIGS. 19 and 20 illustrate an alternative extraction tether 190 of this invention. Tether 190 is in the form of a flexible tube formed of polymer that has an oval cross sectional profile. Two parallel lumens 192 and 194 extend longitudinally through tether 190, (lumens seen in phantom in FIG. 20. A wire 196 extends from the proximal end of bore 192 out through the distal end of tether 190. Wire 196 is coated with a biocompatible insulating material.

As part of the process of preparing the electrode array assembly 40 for deployment, wire 196 is passed through an opening 202 in the proximal end of the assembly foot 52. More particularly, the opening 202 is formed in a section of the assembly wherein carrier 70 is present so that the wire passes through an opening in the carrier. Wire 196 is inserted back into the tether and more particularly lumen 192. The wire is feed through lumen 192 so as to extend out of the proximal end of the tether 190. Thus, parallel sections of wire 196 are located side-by-side, one section in lumen 192 and the other section in the parallel lumen 194. The looping of the wire 196 through opening 202 and the feeing of the wire back in tether lumen 194 releasably attaches tether 190 to the electrode array assembly 40.

Electrode array assembly 40 with attached tether 190 is then disposed in the deployment cannula 150. The electrode array assembly 40 is then deployed over the target tissue as described before. Upon deployment from cannula 150, the assembly foot 52 is not constrained. Therefore, the assembly foot 52, like the assembly head is free to unfold or unroll over the target tissue.

As part of the process of deploying assembly 40, the proximal end of tether 190 is left to extend out of the portal in the body of the patient. At least one end of wire 196 is tied to a terminal integral with power and control unit 156. The opposed end of wire 196 is also tied to a static anchor. This anchor may be attached to the power and control unit 156. The anchor may be a second electrical terminal of the pulse generator.

During the evaluation process, the signals output by the power and control unit 156 are output over wire 196. Wire 196 functions as the antenna over which the signals are broadcast to assembly antenna 54.

As a result of the evaluation process, it may be determined that assembly 40 provides the desired therapeutic effect. Tether 190 is initially disconnected from the assembly 40 by first disconnecting wire 196 from at least one of the anchors (terminals) to which the wire is connected. One end of the wire 196 extending out of the proximal end of the tether 190 is pulled so as to cause the free end of the wire to first be withdrawn through the tether lumen 192 or 194 in which the wire is seated. The wire is then withdrawn from the assembly through assembly opening 202 and out of the second lumen 194 or 192. The withdrawal of wire 196 from assembly bore 202 is the disconnecting of tether 190 from the electrode array assembly 40.

In this described version of the invention, the free end of the wire 196, when it initially travels proximally through tether 190 travels in its own lumen 192 or 194. This eliminates the possibility that the free end of the wire 196 could somehow bind against the adjacent section of wire. If such binding were allowed to occur, it could result in the loop of wire 196 forward of the distal end of the tether 190 simply tightening and pulling the electrode array assembly 40 towards the tether.

Once tether 190 is disconnected from the electrode array assembly 40, a force is applied to the tether to withdraw the tether from the patient.

If, after the evaluation period it is determined that it is necessary to remove the electrode array assembly 40, an extraction tube 130 may be passed over tether 190 and directed towards the assembly. Once the extraction tube is adjacent the electrode array assembly 40 a force is applied to the proximal end of the tether 190. this force causes the tether to pull the electrode array assembly 40 into the extraction tube.

An advantage of this version of the invention is that, the need insert a tool into the body, disconnect the tether 190 from the electrode array assembly 40 is eliminated.

It should be appreciated that, in alternative versions of the above-described embodiment of the invention, a separate conductor, as opposed to wire 196, may function as the tether antenna. In these versions of the invention, the distal end of the tether may have an enlarged head on which the antenna is disposed.

Similarly, in alternative versions of the invention the webs or other members that hold the extraction tether to the electrode array assembly may be integrally part of the electrode array assembly. In these versions of the invention the free ends of the webs, which are spaced from the electrode array assembly 40 are adhesively or mechanically secured to the extraction tether or sleeve.

The shapes of the components may of course differ from what has been described. Thus, there is no obligation that components like the extraction tether or the extraction sleeve always have circular cross sectional profiles. In some versions of the invention it may be desirable to provide an extraction sleeve 64 that has an oval or oblong cross sectional profile. An oval or oblong extraction sleeve 64, could for example have major and minor outer diameters of, respectively, approximately 3.5 and 2.0 mm.

In some versions of the invention, simply pulling on the extraction tether or sleeve may be all that is required to withdraw the electrode array assembly from the tissue against which the assembly is deployed. These versions of the invention eliminate the need to provide an extraction tube.

In versions of the invention wherein the tether is the loop of wire, the associated sleeve may have a single lumen. Alternatively, in some versions of this construction of the invention, there may not even be a need to encase the wire in a sleeve.

Similar in versions of the invention whether the tether includes the loop of wire, the wire may not function as the temporary antenna. In these versions of the invention, wire embedded or routed in the tube, tube 190, performs the antenna function. In some embodiments of these versions of the invention, the wire, in addition to functioning as the mechanical connect to the electrode array assembly functions as the conductor over which signals are supplied from the external unit to the antenna embedded in the tube. Alternatively, conductors separate fro the wire embedded or routed in the tube serve as the elements over which the signals are supplied to the tube antenna.

Therefore, it is the object of the appended claims to cover all such variations and modifications that come within the true spirit and scope of this invention.

What is claimed is:

1. An implantable electrode array assembly, said assembly including:
    a carrier, said carrier adapted for implantation against living tissue inside a body;
    a plurality of electrodes disposed on said carrier, said electrodes designed to flow current through the tissue;
    an array antenna disposed on said carrier for wirelessly receiving or transmitting signals;
    a control circuit disposed on said carrier, said control circuit connected to said electrodes and said array antenna, said control circuit configured to receive signals from said array antenna and, based on the received signals, cause current to be selectively sourced from at least one said electrode and sunk into at least one said electrode;
    a tether that is separate from said carrier, said tether having a section that can be located inside the body so as to be located adjacent the carrier and a section that extends away from the carrier so as to extend out of the body;
    a tether antenna that is separate from said array antenna and that is attached to the section of said tether inside the body and located adjacent said carrier, said tether antenna configured to wirelessly transmit signals to or receive signals from said array antenna;
    a conductor connected to said tether antenna and configured to connect said tether antenna to a device located outside the body; and
    a connector that extends between said tether and said carrier that holds said carrier to said tether so that, when said connector is connected to said tether, the extraction of said tether from the body results in the like extraction of said carrier.

2. The implantable electrode array assembly of claim 1, wherein said tether is in the form of a sleeve that extends circumferentially around at least a portion of said carrier.

3. The implantable electrode array assembly of claim 2, wherein:
    said sleeve has an open distal end; and
    at least one web extends from the distal end of said sleeve to said carrier so as to function as said connector, said at least one web being formed from material that can be severed by a severing tool.

4. The implantable electrode array assembly of claim 1, wherein:
    said connector holds said tether to said carrier so that at least a portion of said tether extends over or under said array antenna; and
    said tether antenna is attached to a portion of said substrate that extends over or under said array antenna.

5. The implantable electrode array assembly of claim 1, wherein:
    said carrier has a distal section on which said electrodes are disposed and a proximal section of which said array antenna is disposed;
    said tether is disposed over said carrier so as to be located proximal to the section on which said electrodes are disposed and extends over or under the section on which said array antenna is disposed; and
    said tether antenna is attached to the portion of said tether that extends over or under the proximal section of said carrier on which said array antenna is disposed.

6. The implantable electrode array assembly of claim 1, wherein said tether antenna is embedded in said tether.

7. The implantable electrode array assembly of claim 1, wherein:
    said tether is formed from an electrically non-conductive material and said tether antenna is embedded in the electrically non-conductive material forming said tether; and
    said connector consists of at least one extension of the electrically non-conductive material forming said tether that extends between said tether and said carrier.

8. The implantable electrode array assembly of claim 7, wherein the at least one extension of said tether that forms said connector: has a loop that extends around a portion of said carrier; or is adhesively secured to said carrier.

9. The implantable electrode array assembly of claim 1, wherein:
    said connector is a wire that is mounted to said tether so that at least a portion of said wire is able to move relative to said tether; and
    the portion of said wire is able to move relative to said tether is looped around a portion of said carrier, wherein the movement of said wire relative to said tether results in the disconnection of said wire from said carrier.

10. The implantable electrode array assembly of claim 1, wherein said carrier has a width and is formed from bendable material so that said carrier can be bent or folded into an insertion cannula that has width smaller than the width of said carrier.

11. An implantable electrode array assembly, said assembly including:
    a carrier configured for implantation against living tissue inside a body;
    a plurality of electrodes disposed on said carrier, said electrodes designed to flow current through the tissue;
    an array antenna disposed on said carrier for wirelessly receiving or transmitting signals;
    a control circuit disposed on said carrier, said control circuit connected to said electrodes and said array antenna, said control circuit configured to receive signals from said array antenna and, based on the received signals, cause current to be selectively sourced from at least one said electrode and sunk into at least one said electrode;
    a tether separate from said carrier, said tether having: a section that is disposed over or under a section of said carrier on which said array antenna is disposed; and a section that extends away from said carrier so as to be located outside the body;
    a tether antenna that is separate from said array antenna, said tether antenna being attached to the section of said tether that is disposed over or under said carrier so that said tether antenna is at least partially disposed over or under said array antenna;

a conductor connected to the tether antenna configured to connect the tether antenna to a device located outside the body; and a connector that extends between said tether and said carrier that holds said carrier to said tether so that, when said connector is connected to said tether, the extraction of said tether from the body results in the like extraction of said carrier.

12. The implantable electrode array assembly of claim 11, wherein said tether is in the form of a sleeve that extends circumferentially around at least a portion of said carrier.

13. The implantable electrode array assembly of claim 12, wherein at least one web extends from the distal end of said sleeve to said carrier so as to function as said connector, said at least one web being formed from material that can be severed by a severing tool.

14. The implantable electrode array assembly of claim 11, wherein:
said carrier has a distal section on which said electrodes are disposed and a proximal section of which said array antenna is disposed;
said tether is disposed over or under said carrier so as to be located proximal to the section on which said electrodes are disposed; and
said tether antenna is attached to the portion of said tether that extends over or under the proximal section of said carrier on which said array antenna is disposed.

15. The implantable electrode array assembly of claim 11, wherein said tether antenna is embedded in said tether.

16. The implantable electrode array assembly of claim 11, wherein:
said tether is formed from an electrically non-conductive material and said tether antenna is embedded in the electrically non-conductive material forming said tether; and
said connector consists of at least one extension of the electrically non-conductive material forming said tether that extends between said connector and said carrier.

17. The implantable electrode array assembly of claim 16, wherein the at least one extension of said tether that forms said connector has a loop that extends around a portion of said carrier or is adhesively secured to said carrier.

18. The implantable electrode array assembly of claim 11, wherein said carrier has a width and is formed from bendable material so that said carrier can be bent or folded into an insertion cannula that has width smaller than the width of said carrier.

19. The implantable electrode array assembly of claim 11, wherein said conductor extends along said tether so as to have a section located outside the body.

20. An implantable electrode array assembly, said assembly including:
a carrier, said carrier configured for implantation against living tissue inside a body;
a plurality of electrodes disposed on said carrier, said electrodes designed to flow current through the tissue;
an array antenna disposed on said carrier for wirelessly receiving or transmitting signals;
a control circuit disposed on said carrier, said control circuit connected to said electrodes and said array antenna, said control circuit configured to receive signals from said array antenna and, based on the received signals, cause current to be selectively sourced from at least one said electrode and sunk into at least one said electrode;
a tether that is separate from said carrier, said tether having a section configured to be located adjacent said carrier in the body and a section that extends away from the body so as to be located outside the body , said tether including a wire that is moveable relative to the section of said tether adjacent said carrier and the section of said tether that extends outside of the body and that extends with said tether outside of the body, said wire having a section that is releasably attached to said carrier, wherein said wire functions as an antenna that transmits signals to or receives signals from said array antenna, and when said wire is attached to said carrier, the extraction of said tether from the body results in the like extraction of said carrier and a disconnected state in which, as a result of the movement of said wire relative to said tether sections, said wire is disconnected from said carrier; and
a conductor connected to said wire that is configured to connect the wire to a device located outside the body.

21. The implantable electrode array assembly of claim 20, wherein:
said tether further includes a flexible member that is formed with at least one bore; and
said wire is looped through the at least one bore of said flexible member so that, within said flexible member, there are plural sections of said wire located side-by-side each other.

22. The implantable electrode array assembly of claim 20, wherein said conductor is an extension of said wire that is mounted to said tether so as to extend outside of the body with said tether.

23. The implantable electrode array assembly of claim 1, wherein said conductor extends along said tether so as to extend out of the body with said tether.

* * * * *